US012564697B2

(12) United States Patent
Dureus

(10) Patent No.: US 12,564,697 B2
(45) Date of Patent: Mar. 3, 2026

(54) BREATHING MASK AND METHODS THEREOF

(71) Applicant: Paul Erby Dureus, Victor, NY (US)

(72) Inventor: Paul Erby Dureus, Victor, NY (US)

(73) Assignee: Gwavision Health & Wellness , LLC, Victor, NY (US)

( * ) Notice: Subject to any disclaimer, the term of this patent is extended or adjusted under 35 U.S.C. 154(b) by 547 days.

(21) Appl. No.: 18/120,415

(22) Filed: Mar. 12, 2023

(65) Prior Publication Data

US 2023/0285706 A1 Sep. 14, 2023

Related U.S. Application Data

(60) Provisional application No. 63/319,769, filed on Mar. 14, 2022.

(51) Int. Cl.
*A61M 16/06* (2006.01)

(52) U.S. Cl.
CPC ................................ *A61M 16/0683* (2013.01)

(58) Field of Classification Search
CPC .......... A61M 16/0683; A61M 16/0066; A61M 16/0833; A61M 16/0605; A61M 16/0633; A61M 16/0875; A61M 16/1065; A61M 2202/0225; A47G 9/1081
See application file for complete search history.

(56) References Cited

U.S. PATENT DOCUMENTS 9,180,269 B2 11/2015 Dureus

FOREIGN PATENT DOCUMENTS

DE 202005008839 U1 * 9/2005 ........ A61M 16/0683

OTHER PUBLICATIONS

Translation of DE 202005008839 (Year: 2005).*

* cited by examiner

*Primary Examiner* — Victoria Murphy
(74) *Attorney, Agent, or Firm* — Jong Patent Firm; Cheng Ning Jong; Tracy P. Jong

(57) ABSTRACT

A breathing mask including an overhead gear assembly including an overhead receptor and a hose attachment connected to the overhead receptor, a patient interface and a pillow surrounding at least a portion of the overhead receptor, the pillow including a back section and two side sections, each side section including an internal groove for accepting a tubing, an outer surface and an inner surface, wherein the hose attachment is positioned outside of a line of sight of the user, when the breathing mask is utilized by the use an elongated connector extending from the overhead receptor to terminate at a terminal end, an elastic loop band connected to the terminal end of the elongated connector and the back section of the pillow, the elastic loop band configured to be disposed around the user's head, wherein the elastic loop band is disposed around the user's head.

20 Claims, 8 Drawing Sheets

BREATHING MASK AND METHODS THEREOF

This non-provisional application claims the benefit of priority from provisional application U.S. Ser. No. 63/319,769 filed on Mar. 14, 2022. Said application is incorporated by reference in its entirety.

BACKGROUND OF THE INVENTION

1. The Field of the Invention

Embodiments of the present disclosure generally relate to a breathing mask and methods thereof. More specifically, embodiments of the present disclosure relate to a breathing mask for alleviating conditions causing sleep apnea or other medical uses and avoiding onset claustrophobia in a patient often caused by a breathing mask.

2. Background Art

Sleep apnea is a biological disorder of the respiratory tract which manifests itself by intensive snoring during sleep. The condition affects particularly the upper airway passages which tend to collapse and become blocked towards the end of every exhalation cycle. Consequently, in order to overcome and avoid suffocation, a patient must exert an effort to continue the breathing process, i.e., the inhalation phase, in which such effort entails the patient's actual awaking. Therefore, the patient is driven into a serious mental and physical condition due to accumulated lack of sleep. Although the patient seems to be asleep, actually he or she is not deriving the benefits of slumber, not to mention the inconvenience caused to people in close proximity.

In the course of medical research, it has been found that great relief is attained if, by some external means, the patient's lungs (and, of course, the upper bronchial passages included) be kept under a constant, slightly elevated air pressure, above the ambient, "atmospheric" pressure.

In the art of respirators, resuscitators, and the like it is well known to provide apparatus in the form of an enclosure which encompasses a portion of the human body such as the upper torso or thoracic region thereof to provide within the confines of the enclosure a pressure containment chamber wherein pressure variations may be applied to the body to stimulate respiration.

It has been known for some time that sleep apnea can be alleviated through the use of respiratory assist apparatus, such as is used in the well-known continuous positive airflow pressure (CPAP) therapy. It is also well recognized that one of the primary causes for patient non-compliance with CPAP or other device therapy is significant physical discomfort cause by the facial masks such devices require.

CPAP therapy essentially requires that air pressure be provided through the patient's nostrils to assist the muscles in the throat to prevent throat blockage during sleep, thus assuaging snoring and actual interruption of breathing. A respirator machine is connected to the patient's nostrils through airflow tubing connected to a facial mask placed over the patient's nose.

There are several known causes of patient concern when prior art apnea therapy masks are in use. For example, physical discomfort can arise with pressure facial neuralgia and vacuum sinusitis. Pressure facial neuralgia is caused by tissue being compressed against the facial bones, for example by a facial mask. Vacuum sinusitis is a painful result of a buildup of pressure in the maxillary cavities located in the maxillary bones located adjacent to the nose. This buildup of pressure is often associated with external pressure placed on the maxillary bones by a facial mask.

What generally goes largely unnoticed, however, in situations where patients have no physical concerns over the use of a mask, significant physiological issues can arise. One major concern is the feeling or sense of claustrophobia when the patient wakes up from a night's sleep and sees a hose coming out of a mask on his/her face. In other situations, the patient wakes up from a night's sleep finding the mask dislodged or imperfectly seated on the patient's face to allow leakages to occur rendering the mask only partially effective at best.

U.S. Pat. No. 9,180,269 to Applicant (hereinafter Dureus) discloses embodiments of breathing masks for alleviating conditions causing sleep apnea and avoiding onset claustrophobia in a patient often caused by a breathing mask. A breathing mask of Dureus comprises an overhead gear assembly comprising an overhead receptor and a hose attachment connected to the overhead receptor and a patient interface coupled to a connector valve of the overhead gear assembly, wherein the hose attachment is positioned outside of a line of sight of a user, when the breathing mask is utilized by the user. While the masks disclosed in Dureus may be suitable for some patients who are able to position themselves in deep sleep or non-rapid eye movement (non-REM) sleep longer where body movements are minimal, dislodgement of the patient interface is still likely in patients who are light sleepers.

Thus, there is a need for an improved breathing mask and at least one method thereof that minimizes leakages from the patient interface.

SUMMARY OF THE INVENTION

In accordance with the present invention, there is provided a breathing mask including:
- (a) an overhead gear assembly including an overhead receptor and a hose attachment connected to the overhead receptor;
- (b) a patient interface;
- (c) a pillow surrounding at least a portion of the overhead receptor, the pillow including a back section for supporting a user's neck and two side sections for supporting two opposing sides of the user's head, each of the side sections including an internal groove for accepting a tubing, the internal groove embedded in each of the side sections, the side sections having an outer surface and an inner surface, wherein the outer surface of the side sections is substantially flat and parallel to the inner surface, wherein the hose attachment is positioned outside of a line of sight of the user, when the breathing mask is utilized by the user;
- (d) an elongated connector extending from the patient interface to terminate at a terminal end; and
- (e) an elastic loop band connected to the terminal end of the elongated connector and the back section of the pillow, the elastic loop band configured to be disposed around the user's head, wherein the elastic loop band is disposed around the user's head with the terminal end of the elongated connector contacting the forehead of the user, securing the patient interface to the user's head and wherein the overhead receptor is adapted to be positioned in substantially the center of a top portion of the user's head.

In one embodiment, the breathing mask further includes a netting extending from the elastic loop band, wherein the netting facilitates use of the elastic loop band over the user's head. In one embodiment, the elastic loop band is configured to be removably connected to the back section of the pillow. In one embodiment, the breathing mask further includes a pair of straps each connecting the back section of the pillow and the patient interface, wherein the pair of straps are disposed around the user's cheeks when in use, further securing the overhead receptor to the user's head. In one embodiment, each of the pair of straps is configured to be removably connected to one of the side sections, allowing each of the straps to be adjustable in length. In one embodiment, the patient interface includes an outflow air pathway for venting the user's exhalations. In one embodiment, the outflow air pathway is directed substantially at an angle that is tangent to a surface through which the outflow air pathway exits the patient interface. In one embodiment, the patient interface includes an outflow air pathway configured to be filtered. In one embodiment, the breathing mask further includes a cushion disposed at the terminal end of the elongated connector to soften contact between the elongated connector and the user's forehead. In one embodiment, the breathing mask further includes an air source coupled to the hose attachment.

In accordance with the present invention, there is further provided a method of administering continuous positive airflow pressure (CPAP) treatment to a patient including: supplying a continuous stream of pressurized air from an air source to the patient utilizing a breathing mask; the breathing mask including: an overhead gear assembly including an overhead receptor and a hose attachment connected to the overhead receptor; a patient interface; and a pillow surrounding at least a portion of the overhead receptor, the pillow including two side sections for supporting two opposing sides of a user's head, each of the side sections including an internal groove for accepting a tubing, the internal groove embedded in each of the side sections, the side sections having an outer surface and an inner surface, wherein the outer surface of the side sections is substantially flat and parallel to the inner surface; wherein the hose attachment is positioned outside of a line of sight of the patient when the breathing mask is utilized by the patient; an elongated connector extending from the overhead receptor to terminate at a terminal end; an elastic loop band connected to the terminal end of the elongated connector and the back section of the pillow, the elastic loop band configured to be disposed around the user's head, wherein the elastic loop band is disposed around the user's head with the terminal end of the elongated connector contacting the forehead of a user, securing the patient interface to the user's head; and wherein the overhead receptor is adapted to be positioned in substantially the center of a top portion of the patient's head.

An object of the present invention is to provide a breathing mask where its patient interface can be securely attached to user or patient's face for its intended use.

Another object of the present invention is to provide a breathing mask that is easy to put on before use and easy to take off after use.

Another object of the present invention is to provide a breathing mask where its patient interface can be securely attached to user or patient's face for its intended use while not significantly appearing in the view of the user so as not to cause a sense of claustrophobia.

Whereas there may be many embodiments of the present invention, each embodiment may meet one or more of the foregoing recited objects in any combination. It is not intended that each embodiment will necessarily meet each objective. Thus, having broadly outlined the more important features of the present invention in order that the detailed description thereof may be better understood, and that the present contribution to the art may be better appreciated, there are, of course, additional features of the present invention that will be described herein and will form a part of the subject matter of this specification.

BRIEF DESCRIPTION OF THE DRAWINGS

So the manner in which the above recited features of the present disclosure can be understood in detail, a more particular description of embodiments of the present disclosure, briefly summarized above, may be had by reference to embodiments, which are illustrated in the appended drawings. It is to be noted, however, the appended drawings illustrate only typical embodiments of embodiments encompassed within the scope of the present disclosure, and, therefore, are not to be considered limiting, for the present disclosure may admit to other equally effective embodiments, wherein.

PARTS LIST

2—breathing mask assembly or breathing mask
4—connector
6—cushion
8—netting
10—elastic loop band
12—attachment strip
14—strap terminated with attaching mechanism
16—overhead gear assembly
18—outflow air pathway or port
20—filter
22—connector tubing and/or valves
24—hose attachment
26—overhead receptor
28—user or patient
30—tangent of surface through which outflow air pathway exits patient interface
32—forehead of user
34—terminal end of a strap portion
36—fastener, e.g., hook and loop fastener
38—internal groove or channel
40—hose 42—neck pillow
44—side pillow
46—terminal end of connector
48—patient interface
50—side of neck pillow
52—blower
54—cushion

PARTICULAR ADVANTAGES OF THE INVENTION

The present breathing mask assembly allows the patient interface to be more securely disposed over a patient's nose and mouth while in use therefore reducing the chance that the benefits offered by the breathing mask assembly will be negated if the patient interface becomes dislodged while in use. In one embodiment, the present breathing mask includes a netting extending from an elastic loop band disposed over a user's head while in use. The netting facilitates the application of the breathing mask as it extends from an upper edge of the elastic loop band to form a network of fabric pieces which hugs the user's head, substantially guiding the manner in which the elastic loop is seated on the user's head in every attempt to put the breathing mask on the user's head. Further, the netting aids in securing the elastic loop band to the user by providing a large surface of contact with the user while allowing air flow through it.

Dureus teaches a breathing mask having no structural elements that would contact a user's forehead while in use. In contrast, a present elastic loop band is useful for securing a connector connected to the patient interface, vastly increasing the securement of the patient interface over the user's nose and mouth while in use.

Figure 1:
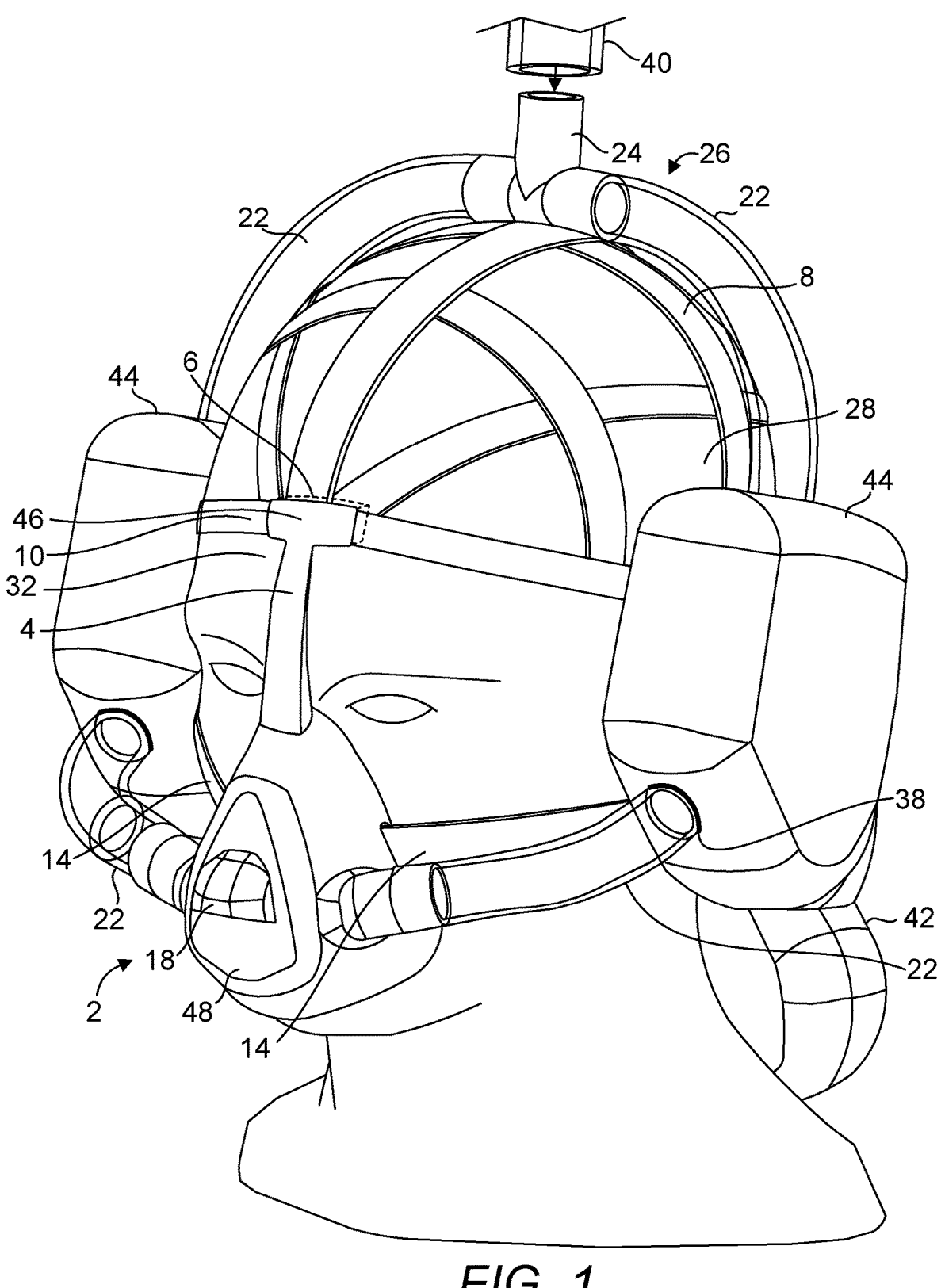
FIG. 1 is a top front perspective view depicting one embodiment of a present breathing mask assembly disposed on a user.

Dureus teaches utilizing bent connector tubings as shown in FIGS. 1.4, 3.1, 3.2, 5.1 and 6.2 of Dureus to allow the tubings to be adapted to the patient interface upon traversing linear internal grooves (204 of Dureus) of pillows (202 of Dureus). The present connector tubings 22 do not feature an inflection point, e.g., a substantial change in the direction of a tubing of at least, e.g., about 10 degrees, in each tubing 22, allowing an air flow through each that is less severely obstructed and where a suitable air pressure can be maintained. Further, without an inflection point in a tubing, the patient interface can be more stably supported as the internal groove useful for securing a portion of the tubing of the overhead receptor is disposed in the form of a curve which resists rotations of a rigid tubing disposed therein, rather than a rectilinear line as one found in Dureus.

In one embodiment, for a user who has been inflicted with a respiratory disease, the exhaled air of a user is diverted onto the patient himself or herself and filtered, lowering the possibility that pathogen-laden streams of air can be spread around without check.

DETAILED DESCRIPTION OF A PREFERRED EMBODIMENT

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

In the following detailed description, numerous specific details are set forth in order to provide an understanding of exemplary embodiments or other examples described herein. In other instances, well-known methods, procedures, and components have not been described in detail, so as to not obscure the following description. Further, the examples disclosed are for exemplary purposes only and other examples may be employed in lieu of, or in combination with, the examples disclosed.

Embodiments of the present disclosure generally relate to a breathing mask and methods thereof. More specifically, embodiments of the present disclosure relate to a breathing mask for alleviating conditions causing sleep apnea while avoiding a sense of claustrophobia. In the following, numerous details are set forth in order to provide an understanding of the embodiments or other examples described herein.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

Exemplary implementations of the present disclosure may include the following benefits and features: a breathing mask that can be used for adapting to any position a patient may move; delivering a secure fit; providing a cost-effective solution; breathable; encourages compliance with a mask protocol; able to provide maximum comfort with effective treatment; or the like. A mask in accordance with exemplary embodiments of the present disclosure may be used to treat sleep apnea, for respiratory treatment, for different breathing procedures, or the like. In accordance with exemplary embodiments of the present disclosure the mask and various components can be combined into a kit with different components necessary for the proper function of the mask, or the like. In accordance with exemplary embodiments of the present disclosure, the mask and system may be easy to use. The system may adapt well to patient movement, may be securely fit to a patient's face, may be breathable with the ability to provide excellent treatment with maximum comfort, or the like. In accordance with exemplary embodiments of the present disclosure, the masks and system may provide various benefits and solve several problems. The pillow and device may support neck muscle with specific pillow designed to fit the user's neck and head. The mask may increase compliance to a treatment program due to the mask's comfortable system of pillows surrounding the user's head or neck, or the like.

In accordance with exemplary embodiments of the present disclosure, the mask may reduce hospital transmitted infection and may be easy to put on or take off. The mask may be therapeutically effective. Many patients who receive treatment for sleep apnea conclude that, although they are satisfied with the continuous positive airflow pressure (CPAP) mask treatment method, they tend to experience discomfort with the current CPAP treatment due to current CPAP designs. Embodiments of the present disclosure may increase patient compliance and help them further enjoy their CPAP mask treatment. In some embodiments, the side pillow 44, such as the side pillows depicted in the FIGS. 1-4, may provide great support and comfort to protect the neck from bending to the side. If the neck of a patient bends to the side, air entry may be reduced when the patient falls asleep.

Embodiments of the present disclosure resist and protect the neck from bending in this manner, preventing this reduction in air entry, or the like.

In accordance with exemplary embodiments of the present disclosure, when someone falls asleep, their body including head and neck tend to be more flaccid and heavier and this mask system supports the head better than conventional CPAP masks or systems. Although described herein as used as a CPAP mask, it is contemplated by and within the present disclosure that the masks of present disclosure may be used as a medical mask for delivery of a gas to the patient, or the like. In conventional systems, when the patient falls asleep their head and neck become flaccid and may cause the head to tilt to the side and obstruct air entry, which can eventually exacerbate the symptoms of sleep apnea. The systems and methods presented herein may substantially prevent that issue by providing support for the head and neck. The systems and methods of the present disclosure may be used in many applications and implementations, for example, they may be used in hospitals and sleep labs, ICUs, CCUs, for anesthesia, private sleep laboratories, or the like.

Some additional uses for the systems and apparatus disclosed herein may include areas where the head or neck should be supported, such as for neck massage, cosmetic purposes, leisure and traveling, or the like. The systems and methods accordance to the present disclosure may help sleep apnea patients, hospitalized patients that require breathing treatment (e.g., daily breathing treatment), intensive care unit (ICU), cardiac care unit (CCU) patients, long distance travelers either by plane, car and boat, or the like. The mask, system, and methods are easy to use and comply with medical protocols. In some embodiments, exemplary apparatus and examples described herein and/or depicted in the figures may be applied or attached to a helmet, or the like. The mask and system disclosed herein may be easy to put on and off a patient's head and may be helpful for use by physicians including surgeons and anesthesiologists, nurses, healthcare professionals, or the like. The mask may provide healthcare professionals, such as doctors, surgeons, nurses, additional room and/or space to perform their work efficiently. Some other implementations of the pillows depicted in the figures may include therapeutic, cosmetic and traveling uses, or situations where it is desirable to provide neck and/or head support, or the like.

Patients and healthcare professionals are always searching for new solutions that are beneficial to their care. They are always looking for authentic solutions that can provide better care with maximum treatment delivery and comfort. The mask and system are designed to be easy to use, cost effective to produce. In accordance with exemplary embodiments, the mask has a pillow system to help with maximum comfort treatment delivery. It also helps with better facial seal to prevent air leakage and to support the neck in place.

Figure 2:
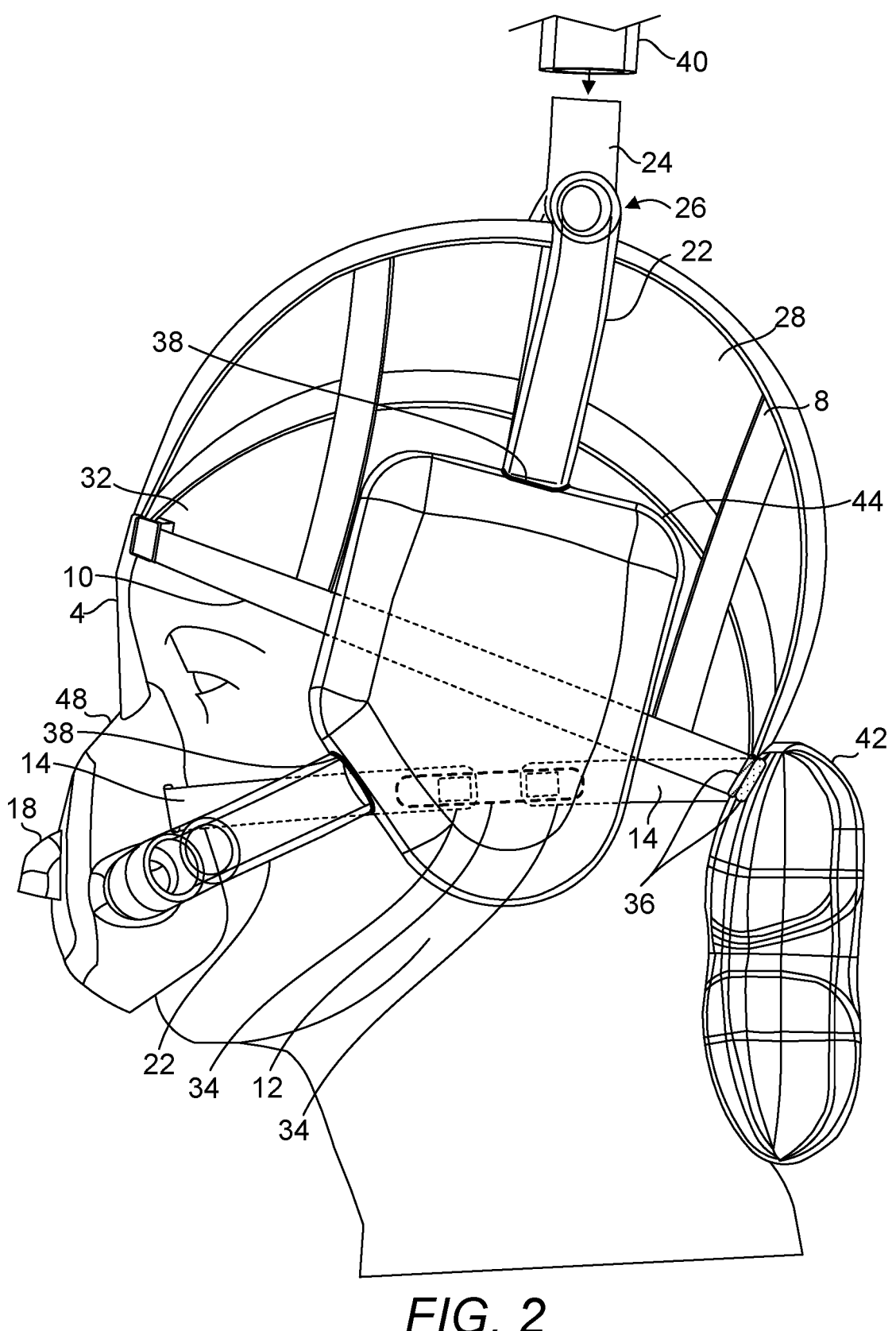
FIG. 2 is a side view depicting one embodiment of a present breathing mask assembly disposed on a user.
Figure 3:
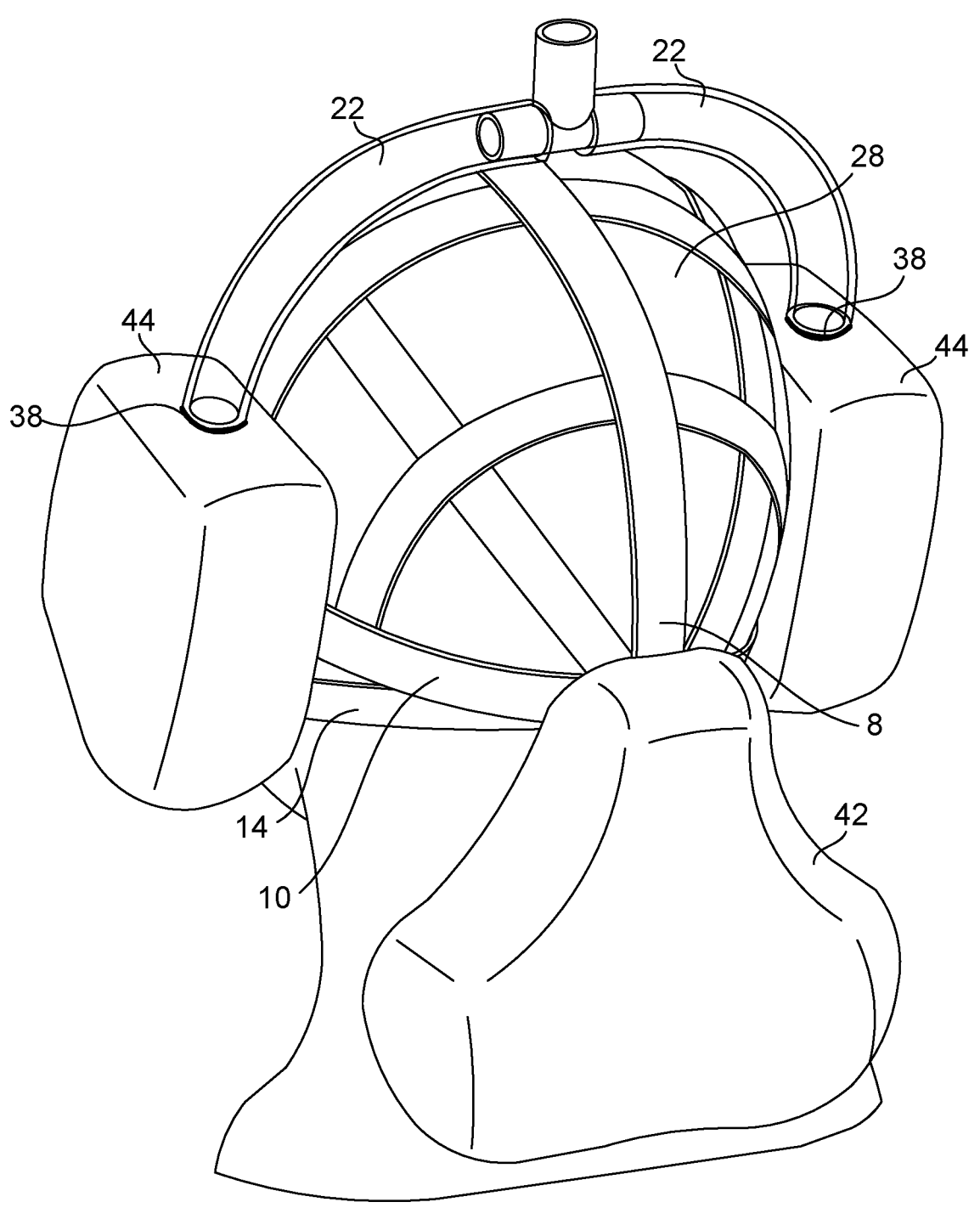
FIG. 3 is a top rear perspective view depicting one embodiment of a present breathing mask assembly disposed on a user.
Figure 4:
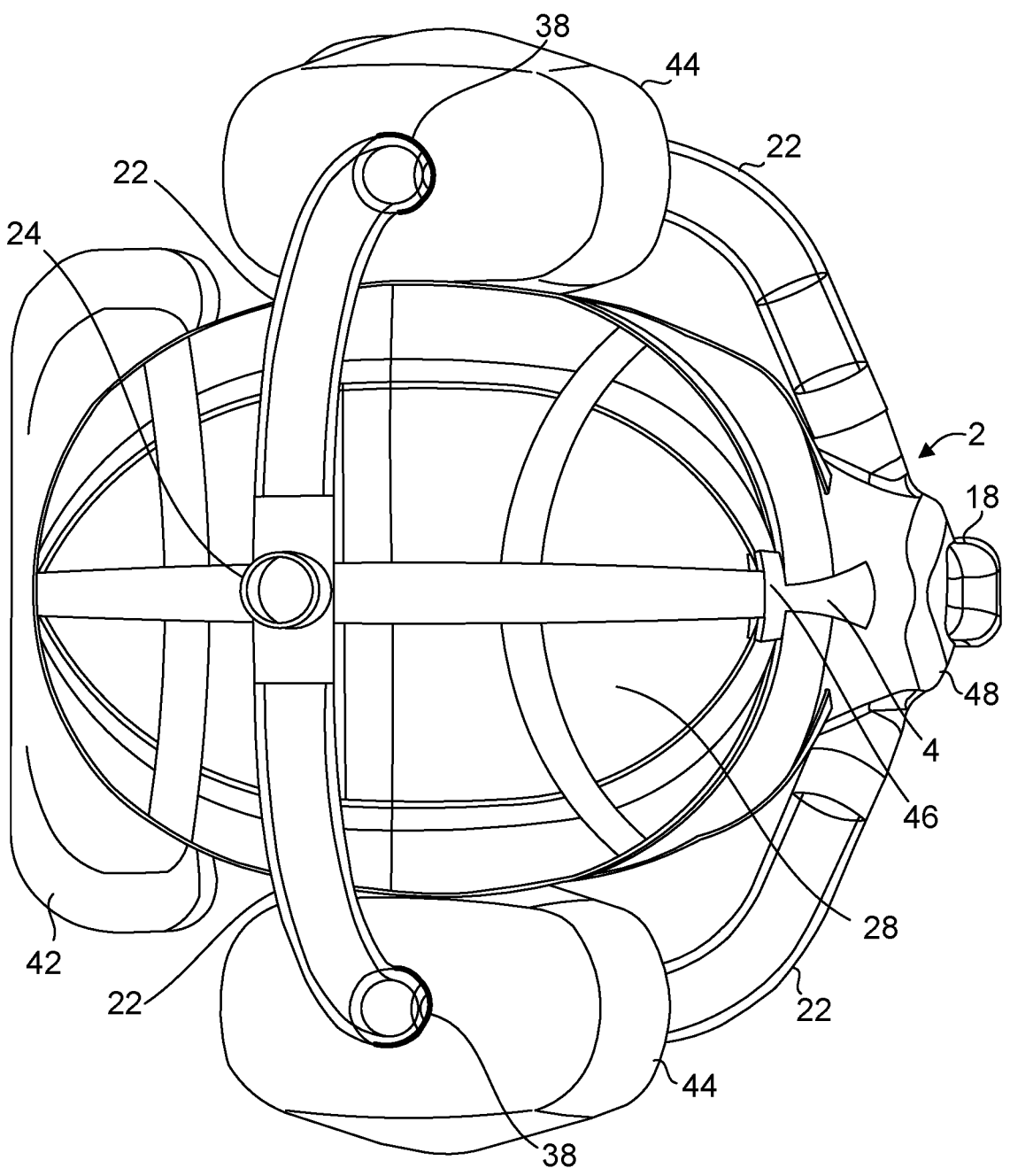
FIG. 4 is a top view depicting one embodiment of a present breathing mask assembly disposed on a user.

FIG. 1 is a top front perspective view depicting one embodiment of a present breathing mask assembly or breathing mask 2 disposed on a user 28. FIG. 2 is a side view depicting one embodiment of a present breathing mask assembly disposed on a user 28. FIG. 3 is a top rear perspective view depicting one embodiment of a present breathing mask assembly disposed on a user 28. FIG. 4 is a top view depicting one embodiment of a present breathing mask assembly disposed on a user 28. The breathing mask 2 includes an overhead gear assembly 16, a patient interface 48, a pillow 42, 44 surrounding at least a portion of the overhead receptor 26, an elongated connector 4 extending from the patient interface 48 to terminate at a terminal end 46 and an elastic loop band 10 connected to the terminal end 46 of the elongated connector 4 and the neck pillow 42, the elastic loop band 10 configured to be disposed around the user's head. The side pillow 44 of the pillow may generally be positioned on a patient's face comfortably, for example, by leaving room for the patient's ear, thus ensuring greater patient comfort. The side pillows 44 and the neck pillow 42 are generally viewed collectively as a neck support pillow and the side pillows 44 may be considered as the side sections of the neck support pillow and the neck pillow 42 as the back section of the neck support pillow or simply, pillow. In one embodiment, the breathing mask further includes a cushion 6 disposed at the terminal end of the elongated connector to soften contact between the elongated connector 4 and the user's forehead 32. The overhead gear assembly 16 includes an overhead receptor 26 and a hose attachment 24 connected to the overhead receptor 26. The pillow includes a neck pillow 42 for supporting a user's neck and two side pillows 44 for supporting two opposing sides of the user's head, each of the side pillows 44 including an internal groove 38 for accepting a tubing, the internal groove 38 embedded in each of the side pillows 44, the side pillows 44 having an outer surface and an inner surface, wherein the outer surface of the side pillows is substantially flat and parallel to the inner surface, wherein the hose attachment 24 is positioned outside of a line of sight of the user, when the breathing mask is utilized by the user 28. The elastic loop band 10 is disposed around the user's head with the terminal end of the elongated connector contacting the forehead 32 of a user, securing the patient interface 48 to the user's head. The overhead receptor 26 is adapted to be positioned in substantially the center of a top portion of the user's head. A side pillow 44 or the neck pillow 42 may be made of a cushion-like or absorbent material, such as foam, cotton, down feathers, or the like, and is adjustable to different temperatures to accommodate each patient's needs.

In one embodiment, the breathing mask 2 further includes an air source coupled to the hose attachment 24 and supplied via a hose 40. The hose 40 may generally be attached to the hose attachment 24 atop the patient's head, outside of patient's view. In many embodiments of the present disclosure, by keeping the hose 40 out of the patient's view, there is minimal likelihood the patient will awake during the night and immediately feel claustrophobic, or a similar fear, due to the hose or tubes 22 entering the patient interface 48.

In one embodiment, the breathing mask 2 further includes a netting 8 extending from the elastic loop band 10, wherein the netting 8 facilitates use of the elastic loop band 10 over the user's head. In one embodiment, the elastic loop band 10 is configured to be removably connected to the neck pillow 42, e.g., using a hook and loop fastener 36. This way, the user has the freedom to choose another pillow for use as the neck pillow 42 can be detached to be cleaned. Further, in another embodiment not shown, the netting material shown may be replaced with another material as long as the netting 8 material remains pliable and breathable while still aiding in securing the elastic loop band 10 to the user 28.

In one embodiment, the breathing mask 2 further includes a pair of straps 14 each connecting the neck pillow 42 and the patient interface 48, wherein the pair of straps 14 are disposed around the user's cheeks when in use, further securing the patient interface 48 to the user's head. In one embodiment, each of the pair of straps 14 is configured to be removably connected to one of the side pillows 44, allowing each of the straps to be adjustable in length. As shown in FIG. 2, an attachment strip 12 is attached on the inner surface of a side pillow 44, the attachment strip 12 serves as band along which portions of a strap 14 can be adjusted.

Complementary attaching mechanisms, e.g., hook or loop portions may be disposed on the terminal ends 34 of the portions which make up a strap 14. For instance, if a loop portion is disposed on the attachment strip 12, each portion of a strap 14 will be terminated with a hook portion and vice versa. For some patients, these straps 14 may not be required or desired and they may be configured to be removably attachable to the patient interface 48 as well as the neck pillow 42 by attachment means commonly used in the medical device industry.

Figure 5:
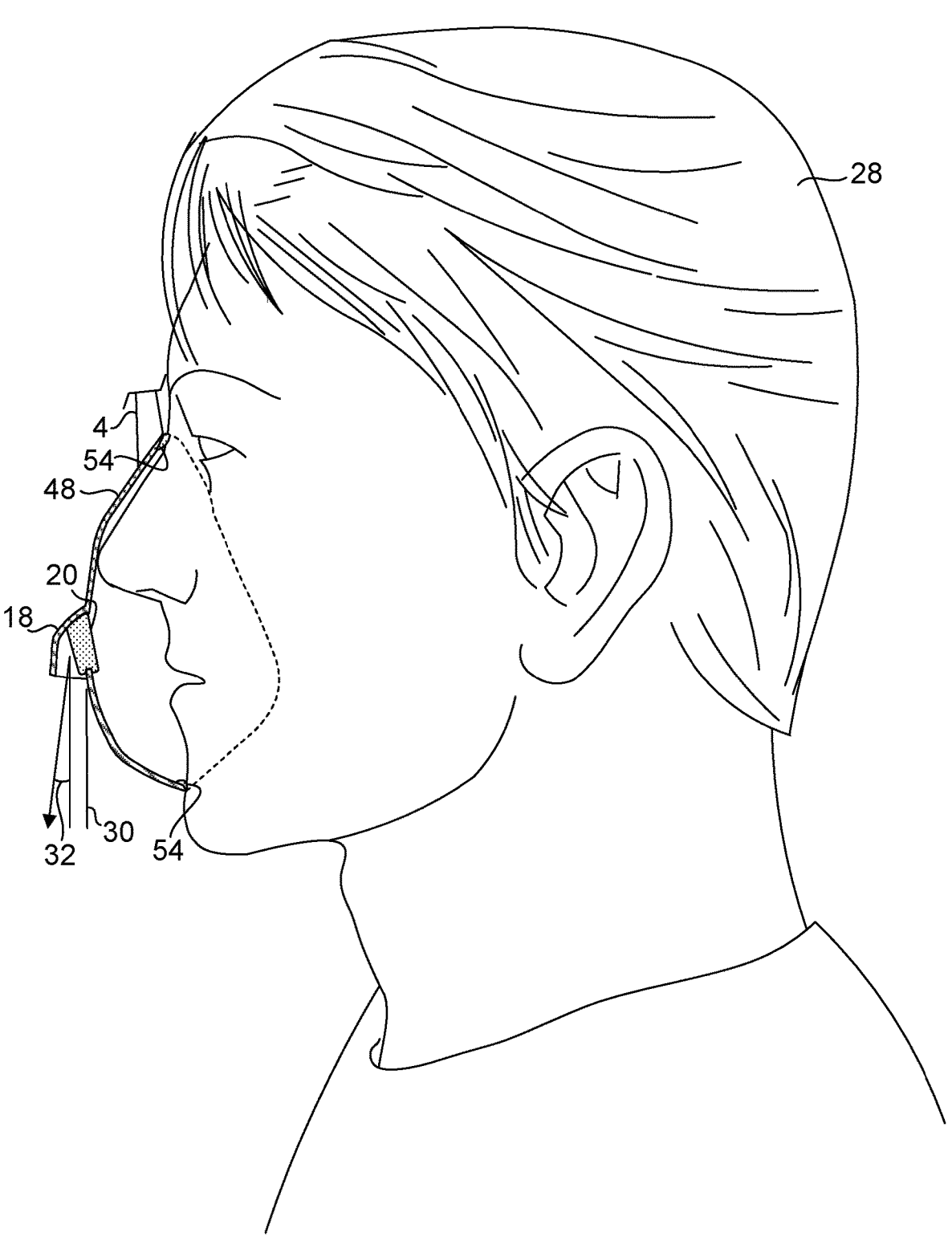
FIG. 5 is a side cross-sectional view a patient interface, depicting an outflow air pathway of the patient interface and a filter disposed therein.

FIG. 5 is a side cross-sectional view a patient interface 48, depicting an outflow air pathway 18 of the patient interface 48 and a filter 20 disposed therein. The patient interface 48 includes an outflow air pathway 18 for venting the user's exhalations. In the embodiment shown, the outflow air pathway 18 is directed substantially at an angle that is tangent 30 to a surface through which the outflow air pathway exits the patient interface 48. In the embodiment shown, a cushion 54 is disposed about the periphery of the patient interface 48 to provide an enhanced seal to reduce leakage through the periphery of the patient interface 48, diminish skin irritation to the user 28, allow proper adjustment of the patient interface 48 over the user's nose and mouth as well as making the patient interface 48 more tolerable for use by the user.

In the embodiment shown, the patient interface 48 includes an outflow air pathway 18 configured to be filtered using a filter 20 interposed between the cavity of the patient interface 48 and the outflow air pathway 18.

Figure 6:
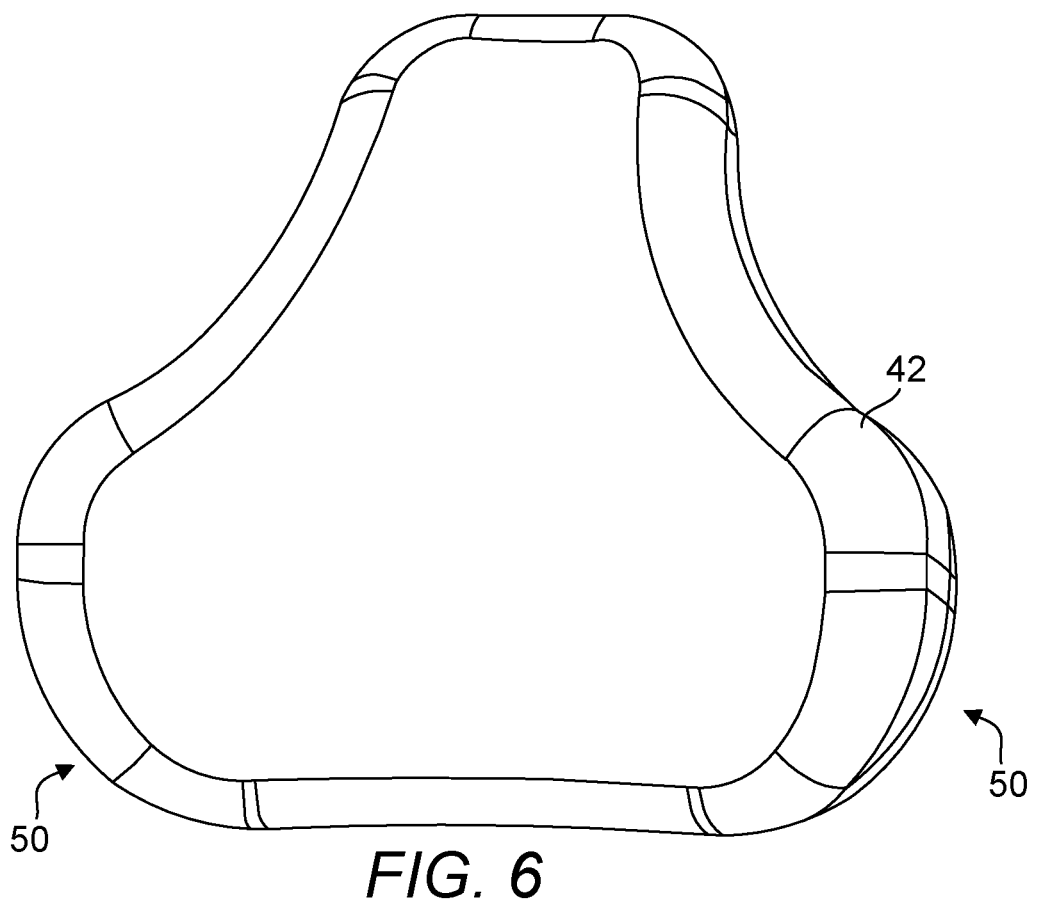
FIG. 6 is a front view depicting one embodiment of a neck pillow of a present breathing mask assembly.
Figure 7:
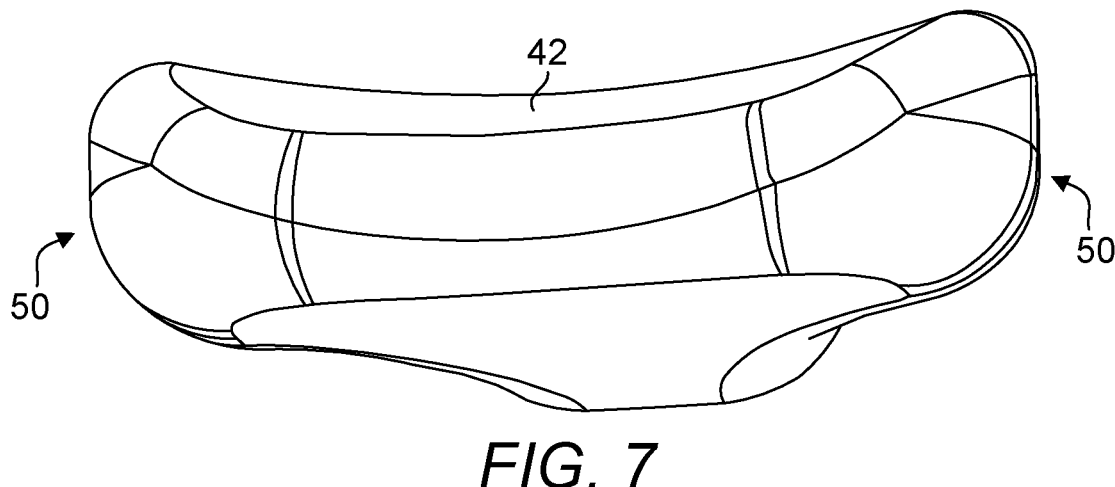
FIG. 7 is a bottom view depicting one embodiment of a neck pillow of a present breathing mask assembly.

FIG. 6 is a front view depicting one embodiment of a neck pillow 42 of a present breathing mask assembly. FIG. 7 is a bottom view depicting one embodiment of a neck pillow 42 of a present breathing mask assembly. It shall be noted that sufficient materials are disposed on two sides 50 of the neck pillow 42, flanking the user's neck while the neck pillow 42 is in use, to reduce the tendency of the user 28 from rolling off the neck pillow 42 when the user's head and neck become flaccid.

Figure 8:
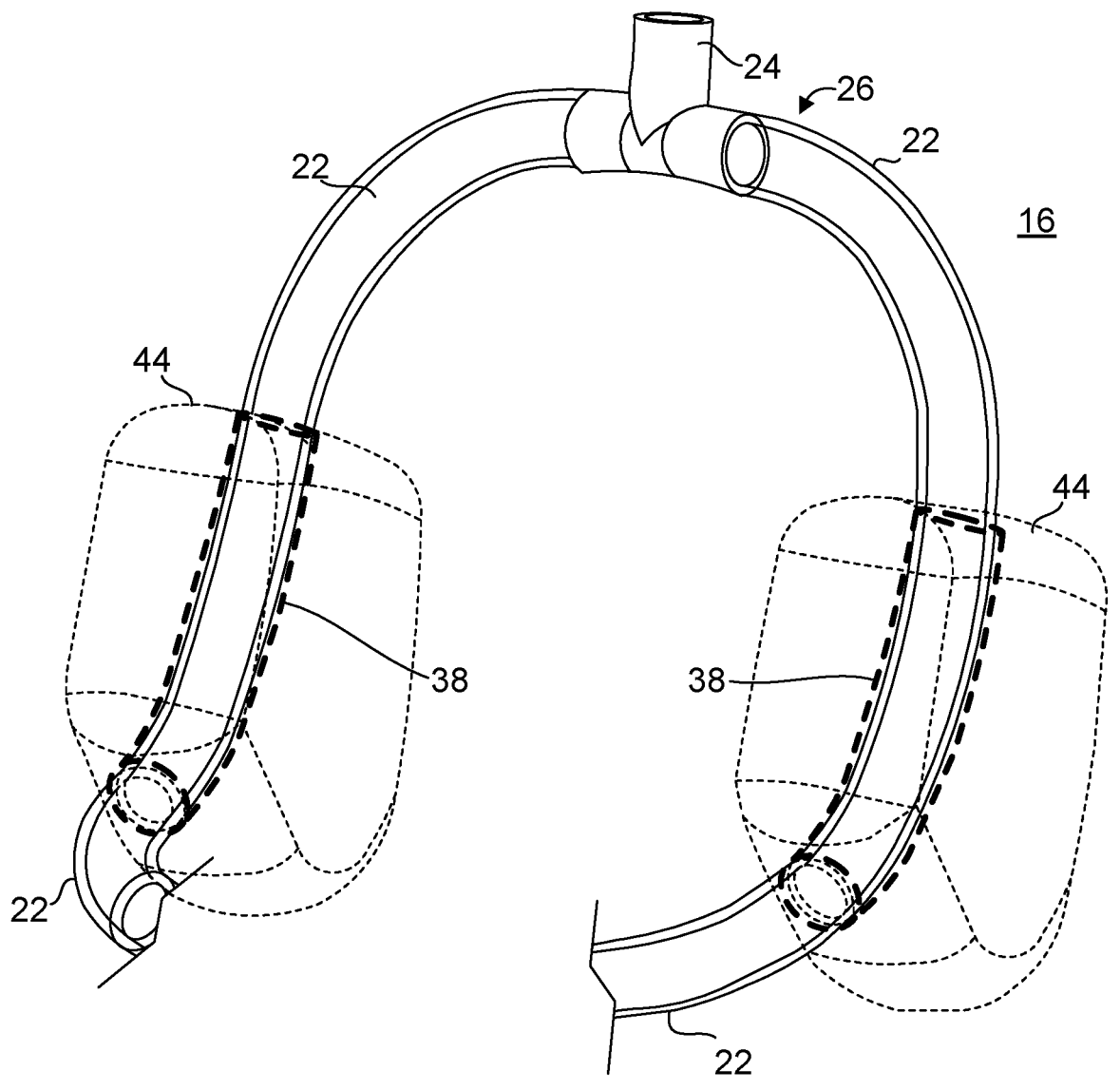
FIG. 8 depicts a frontal view of an overhead gear assembly in accordance with one embodiment of the present disclosure.

FIG. 8 depicts a frontal view of an overhead gear assembly 16 in accordance with one embodiment of the present disclosure. The overhead gear assembly 16 as shown includes the overhead receptor 26 and a hose attachment 24. The overhead receptor 26 extends to the left and to the right with a connector tubing at each end for connection with a patient interface (not shown). The overhead receptor 26 may be adjustable depending on the size of the patient's head. The hose attachment 24 gives a hose mobility to allow for the patient to move freely from side to side without any discomfort. The hose attachment 24 ensures the hose will be in a ponytail position atop the patient's head, or alternatively, in a position away from the patient's face to retain the patient's ability to move freely from side to side without the patient feeling suffocated or claustrophobic. The hose attachment 24 may generally connect to a blower (not shown), or other air/oxygen source. One significant advantage of this assembly provides that the individual is able to move freely throughout the night while the mask and overhead gear assembly 16 is left in place either preferably with a connection to the blower detached via hose 40 at hose attachment 24 and reattached when the blower is again required. The connector tubing and/or valves 22 at the ends of the overhead receptor 26 generally attach to a patient interface (not shown). In operation, before sleeping, a user places the breathing mask apparatus on his/her head so that the hole in the apparatus through which air is transferred is placed directly over the user's nasal passages. The blower (not shown) is then activated, producing a positive air pressure on the user's airways by forcing air into the user's nasal passages, thus keeping them open throughout the night and increasing the ease of breathing which is hindered by obstructive sleep apnea. The amount of air pressure provided by the blower may be adjusted by the user and may be set to comply with the advice of a medical practitioner or health care specialist.

As appreciated by embodiments of the present disclosure, acceptable materials for components of the present disclosure may comprise any suitable material as understood by those of ordinary skill in the art. More specifically, acceptable materials may comprise any material recognized by government agencies monitoring medical or health devices, including the Food and Drug Administration (FDA), the Center for Disease Control (CDC), the Environmental Protection Agency (EPA). Generally, embodiments of the present disclosure may comprise any polymer, metal, fabric, or the like, as commonly used by hospitals and/or medical device manufacturers.

Figure 9:
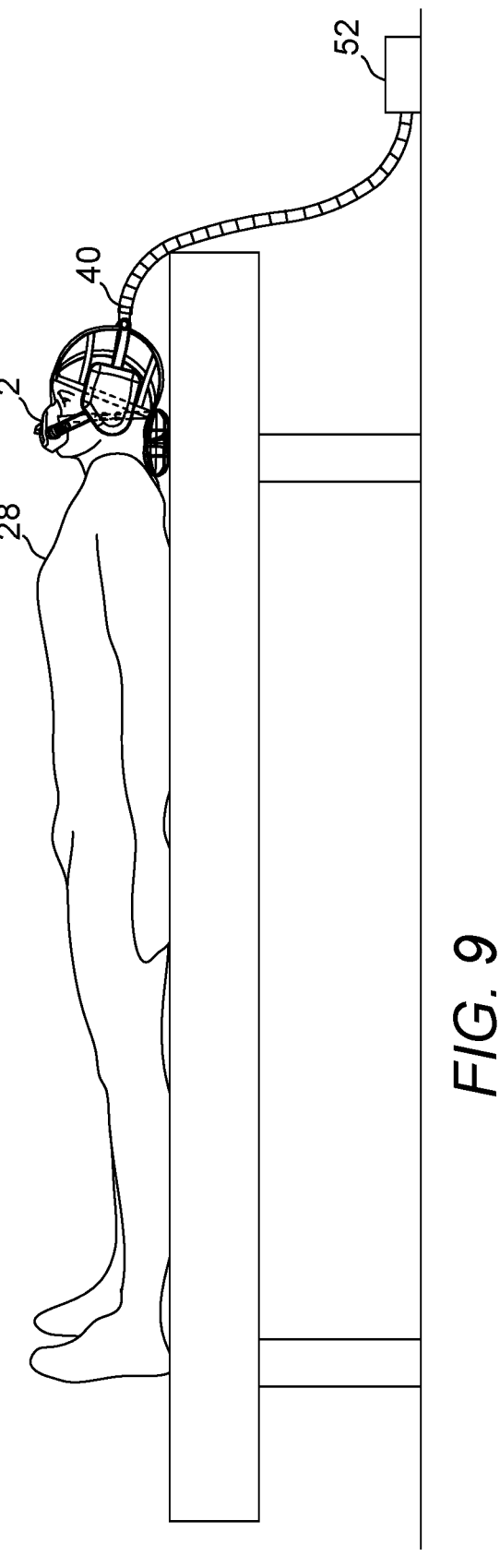
FIG. 9 illustrates a patient in a supine position utilizing a breathing mask assembly in accordance with one embodiment of the present disclosure.

FIG. 9 illustrates a patient in a supine position utilizing a breathing mask assembly 2 in accordance with one embodiment of the present disclosure. The breathing mask 2 may generally be connected to a blower 52, or other air source, for providing the increased air flow to the patient 28 via hose 40.

The detailed description refers to the accompanying drawings that show, by way of illustration, specific aspects and embodiments in which the present disclosed embodiments may be practiced. These embodiments are described in sufficient detail to enable those skilled in the art to practice aspects of the present invention. Other embodiments may be utilized, and changes may be made without departing from the scope of the disclosed embodiments. The various embodiments can be combined with one or more other embodiments to form new embodiments. The detailed description is, therefore, not to be taken in a limiting sense, and the scope of the present invention is defined only by the appended claims, with the full scope of equivalents to which they may be entitled. It will be appreciated by those of ordinary skill in the art that any arrangement that is calculated to achieve the same purpose may be substituted for the specific embodiments shown. This application is intended to cover any adaptations or variations of embodiments of the present invention. It is to be understood that the above description is intended to be illustrative, and not restrictive, and that the phraseology or terminology employed herein is for the purpose of description and not of limitation. Combinations of the above embodiments and other embodiments will be apparent to those of skill in the art upon studying the above description. The scope of the present disclosed embodiments includes any other applications in which embodiments of the above structures and fabrication methods are used. The scope of the embodiments should be determined with reference to the appended claims, along with the full scope of equivalents to which such claims are entitled.

What is claimed herein is:

1. A breathing mask comprising:

(a) an overhead gear assembly comprising an overhead receptor and a hose attachment connected to the overhead receptor;

(b) a patient interface;

(c) a pillow surrounding at least a portion of the overhead receptor, the pillow comprising a back section for supporting a user's neck and two side sections for supporting two opposing sides of the user's head, each of the side sections comprising an internal groove for accepting a tubing, the internal groove embedded in each of the side sections, the side sections having an outer surface and an inner surface, wherein the outer surface of the side sections is substantially flat and parallel to the inner surface, wherein the hose attachment is positioned outside of a line of sight of the user, when the breathing mask is utilized by the user;

(d) an elongated connector extending from the patient interface to terminate at a terminal end; and (e) an elastic loop band connected to the terminal end of the elongated connector and the back section of the pillow, the elastic loop band configured to be disposed around the user's head, wherein the elastic loop band is configured to be disposed around the user's head with the terminal end of the elongated connector configured to contact the forehead of the user thereby securing the patient interface to the user's head and wherein the overhead receptor is adapted to be positioned in substantially the center of a top portion of the user's head.

2. The breathing mask of claim 1, further comprising a netting extending from the elastic loop band, wherein the netting is configured to facilitate use of the elastic loop band over the user's head.

3. The breathing mask of claim 1, wherein the elastic loop band is configured to be removably connected to the back section of the pillow.

4. The breathing mask of claim 1, further comprising a pair of straps each connecting the back section of the pillow and the patient interface, wherein the pair of straps are configured to be disposed around the user's cheeks when in use, further securing the patient interface to the user's head.

5. The breathing mask of claim 4, wherein each of said pair of straps is configured to be removably connected to one of the side sections, allowing each strap of said pair of straps to be adjustable in length.

6. The breathing mask of claim 1, wherein the patient interface comprises an outflow air pathway for venting the user's exhalations.

7. The breathing mask of claim 6, wherein the outflow air pathway is directed substantially at an angle that is tangent to a surface through which the outflow air pathway exits the patient interface.

8. The breathing mask of claim 1, wherein the patient interface comprises an outflow air pathway configured to be filtered.

9. The breathing mask of claim 1, further comprising a cushion disposed at the terminal end of the elongated connector to soften contact between the elongated connector and the user's forehead.

10. The breathing mask of claim 1, further comprising an air source coupled to the hose attachment.

11. A method of administering continuous positive airflow pressure (CPAP) treatment to a patient comprising: supplying a continuous stream of pressurized air from an air source to the patient utilizing a breathing mask; the breathing mask comprising: an overhead gear assembly comprising an overhead receptor and a hose attachment connected to the overhead receptor; a patient interface; and a pillow surrounding at least a portion of the overhead receptor, the pillow comprising two side sections for supporting two opposing sides of a user's head, each of the side sections comprising an internal groove for accepting a tubing, the internal groove embedded in each of the side sections, the side sections having an outer surface and an inner surface, wherein the outer surface of the side sections is substantially flat and parallel to the inner surface; wherein the hose attachment is positioned outside of a line of sight of the patient when the breathing mask is utilized by the patient; an elongated connector extending from the patient interface to terminate at a terminal end; an elastic loop band connected to the terminal end of the elongated connector and the back section of the pillow, the elastic loop band configured to be disposed around the user's head, wherein the elastic loop band is disposed around the user's head with the terminal end of the elongated connector contacting the forehead of a user, securing the patient interface to the user's head; and wherein the overhead receptor is adapted to be positioned in substantially the center of a top portion of the patient's head.

12. The method of claim 11, wherein the breathing mask further comprises a pair of straps each connecting the back section of the pillow and the patient interface, wherein the pair of straps are disposed around the user's cheeks when in use, further securing the patient interface to the user's head.

13. The method of claim 12, wherein each of said pair of straps is configured to be removably connected to one of the side sections, allowing each said strap to be adjustable in length.

14. The method of claim 11, wherein the breathing mask further comprises a cushion disposed at the terminal end of the elongated connector to soften contact between the elongated connector and the user's forehead.

15. The method of claim 11, wherein the breathing mask further comprises a netting extending from the elastic loop band, wherein the netting facilitates use of the elastic loop band over the user's head.

16. The method of claim 11, wherein the elastic loop band is configured to be removably connected to the back section of the pillow.

17. The method of claim 11, wherein the patient interface comprises an outflow air pathway for venting the user's exhalations.

18. The method of claim 17, wherein the outflow air pathway is directed substantially at an angle that is tangent to a surface through which the outflow air pathway exits the patient interface.

19. The method of claim 11, wherein the patient interface comprises an outflow air pathway configured to be filtered.

20. The method of claim 11, wherein the breathing mask further comprises the air source coupled to the hose attachment.

* * * * *